US00PP20475P3

(12) United States Plant Patent
Blom

(10) Patent No.: US PP20,475 P3
(45) Date of Patent: Nov. 10, 2009

(54) ***CHRYSANTHEMUM* PLANT NAMED 'ZANMUSUNSET'**

(50) Latin Name: *Chrysanthemum×morifolium*
Varietal Denomination: Zanmusunset

(75) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 12/003,567

(22) Filed: Dec. 28, 2007

(65) Prior Publication Data

US 2009/0172853 P1 Jul. 2, 2009

(51) Int. Cl.
*A01H 5/00* (2006.01)

(52) U.S. Cl. ..... Plt./290

(58) Field of Classification Search ..... Plt./290
See application file for complete search history.

*Primary Examiner*—David H Kruse
*Assistant Examiner*—June Hwu

(74) *Attorney, Agent, or Firm*—Steptoe & Johnson LLP

(57) ABSTRACT

A *chrysanthemum* plant named 'Zanmusunset' characterized by its medium sized blooms with orange ray florets and prolific branching; natural season flower date September 14; blooming for a period of 5 weeks.

3 Drawing Sheets

Botanical designation: *Chrysanthemum×morifolium* Ramat.

Cultivar denomination: 'Zanmusunset'.

BACKGROUND OF THE INVENTION

The present invention relates to a new and distinct cultivar of *chrysanthemum* plant, botanically known as *Chrysanthemum×morifolium* Ramat., commercially known as a garden mum, and herein after referred to by the cultivar denomination 'Zanmusunset'. 'Zanmusunset' is a product of a breeding and selection program for outdoor pot mums (garden mums) which had the objective of creating new *chrysanthemum* cultivars with a double type flower, a natural season flower date around September 14 (week 37); blooming for a period of 5 weeks. 'Zanmusunset' is a seedling resulting from a crossing of the seed parent id 996 and pollen parent id 4422. Plants of the new cultivar 'Zanmusunset' differ from its parent plants in (1) flower type and (2) plant vigor. (1) The flower type of the seed parent and of 'Zanmusunset' is double, while that of the male parent is semi-double. (2) The plants of the male parent are more strongly vigorous than those of 'Zanmusunset' and of its seed parent.

The new and distinct cultivar was discovered and selected as a flowering plant by Wilhelmus Bemardus Blom on a cultivated field in Rijsenhout, The Netherlands in 2005. The first act of asexual production of 'Zanmusunset' was accomplished when vegetative cuttings from the initial selection in 2005 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
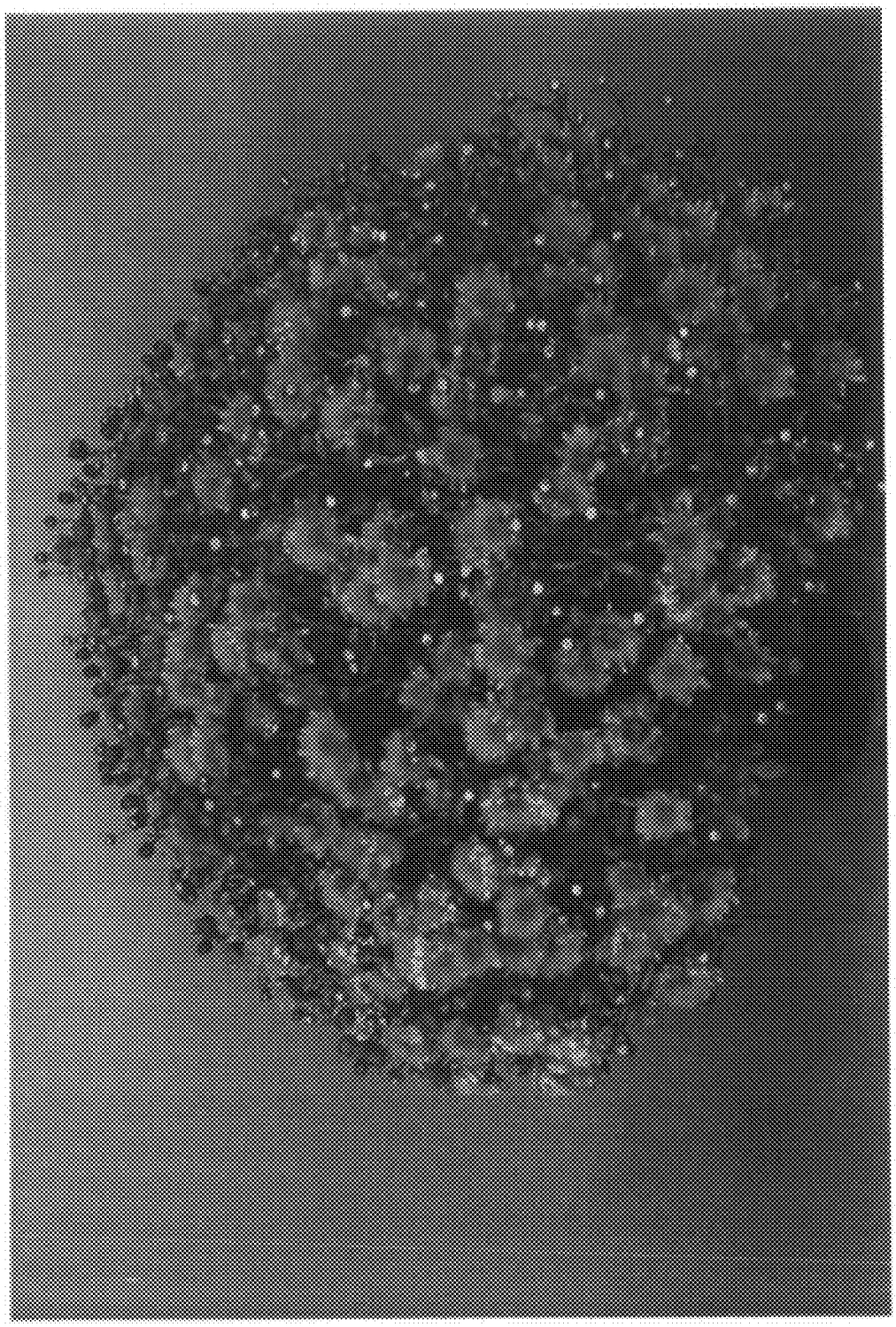
FIG. 1 shows a plant of the cultivar in full bloom.
Figure 2:
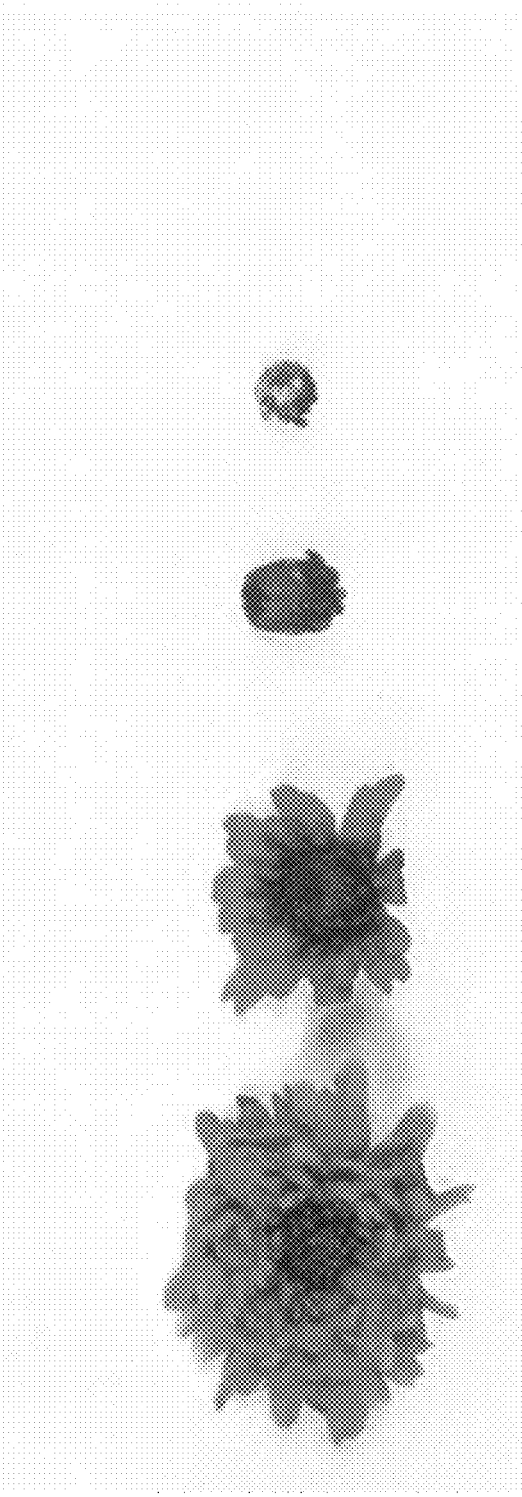
FIG. 2 shows the various stages of bloom of the new cultivar.
Figure 3:
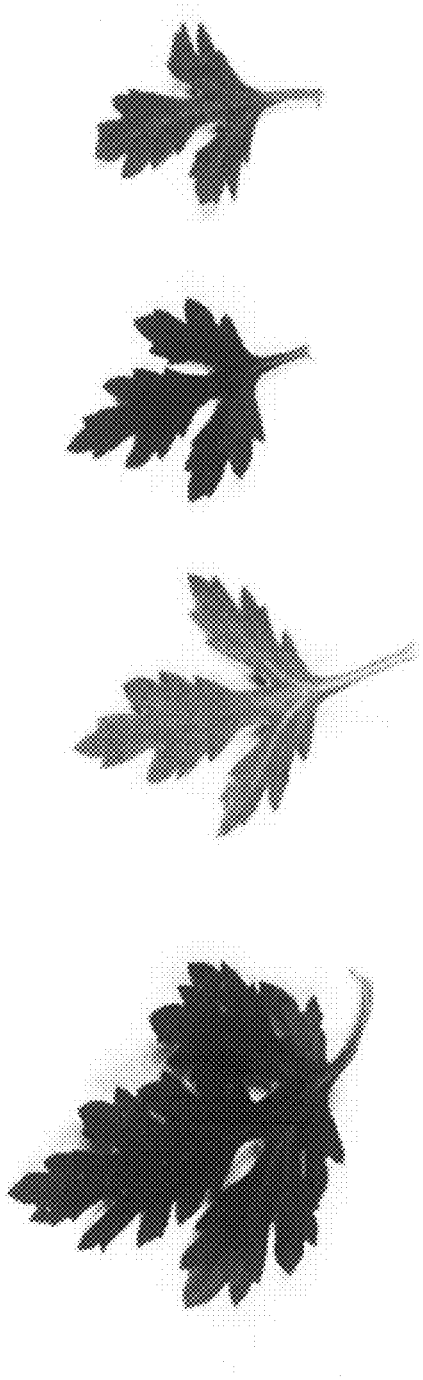
FIG. 3 shows the various stages of foliage of the new cultivar.

The observations and measurements were gathered from plants grown out door in Rijsenhout, The Netherlands under natural day length and temperature and planted in week 25 in 2007. The natural blooming date of this crop was September 14 (week 37). The average height of the plants was 40–45 cm. No growth retardants were used. No tests were done on disease or insect resistance or susceptibility. No tests were done on cold or drought tolerance. This new variety produces medium sized blooms with orange ray florets blooming for a period of 5 weeks.

From the cultivars known to inventor the most similar existing cultivar in comparison to 'Zanmusunset' is 'Thor' (U.S. Plant Pat. No. 12,597). When 'Thor' and 'Zanmusunset' are being compared the following differences are noticed: The differences of 'Thor' and 'Zanmusunset' are (1) Flower size and (2) Plant size. (1) The flowers of 'Zanmusunset' are smaller in size than those of 'Thor'. (2) The plants of 'Zanmusunset' are larger than those of 'Thor'.

The following is a description of the plant and characteristics that distinguish 'Zanmusunset' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

| Botanical description of *chrysanthemum* plant named 'Zanmusunset' | |
|---|---|
| Bud | |
| Size | Small; cross-section 1 cm, height 0.8 cm |
| Outside Color | Greyed-orange 168D |
| Phyllaries | 2 rows |
| Phyllaries among disc-florets | Not present |
| Bloom | |
| Type | Double |
| Height | 1 cm |
| Size | 4.5 cm |
| Phyllary number | 25-28 |
| Phyllary color (upper surface) | Green 138A |
| Phyllary length and width | 7 mm and 3 mm |
| Peduncle length | 12-14 cm |
| Peduncle color | Green 139C |
| Number of blooms per branch | Approx. 6 blooms per branch |
| Duration of flowering | 5 weeks |
| Seeds | Produced in small quantities, ovate grey-brown 199A, 1 ½ mm in length. |
| Fragrance | Typical *chrysanthemum,* slightly |
| Color | |
| Center of the flower | Immature stage: Greyed-red 181A<br>Mature stage: Greyed-orange 168C |
| Color of upper surface of the ray-florets | Greyed-orange 168 B-C |
| Color of the lower surface of the ray-florets | Greyed-orange 173C |
| Tonality from Distance | A garden mum with orange flowers |
| Color of the ray-florets after aging of the plant | Greyed-orange 167D |
| Ray florets | |
| Texture | Upper and under surface smooth |
| Number | 220-230 |
| Cross-section | Flat |
| Longitudinal axis of majority | Straight |
| Length of corolla tube | 0.5 cm |
| Ray-floret margin | Entire |
| Ray-floret length | 1.8-2.5 cm |
| Ray-floret width | 0.3-0.5 cm |
| Ratio length/width | High |
| Shape of tip | Dentate |
| Disc florets | Absent |
| Receptacle shape | Conical raised |
| Reproductive Organs | |
| Stamen | Absent |
| Pistil | Present in ray-florets (one per ray-floret) |
| Style color | Yellow 13A |
| Style Length | 3 mm |
| Stigma color | Yellow-green 144A |
| Stigma Width | 1 mm |
| Ovaries | Enclosed in calyx |

TABLE 1-continued

| Botanical description of *chrysanthemum* plant named 'Zanmusunset' | |
|---|---|
| Plant | |
| Form | Grown as a spray type potmum, outdoor mounded and round |
| Growth habit | Spherical shape |
| Growth rate | Vigorous |
| Height | 40-45 cm |
| Width | 55 cm |
| Stem Color | Greyed-brown 199C |
| Stem Strength | Strong |
| Stem Brittleness | Not brittle |
| Stem Anthocyanin Coloration | Absent |
| Internode length | 1-1.5 cm |
| Length of lateral branch | From top to bottom 20-22 cm |
| Lateral branch color | Yellow-green 146D |
| Lateral branch, attachment | Medium strength |
| Branching (average number of lateral branches) | Prolific with 8 breaks after pinching |
| Natural season blooming date | September 14 (week 37) |
| Foliage | |
| Leaf color | Upper side: Green 139 A-B<br>Lower side: Green 138A |
| Color midvein | Upper side: Yellow-green 147D<br>Lower side: Yellow-green 148D |
| Size | Small.; length 4.5-7 cm, width 3-5 cm |
| Quantity (number per lateral branch) | 23-25 |
| Shape | Ovate |
| Texture upper side | Glabrous |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Converging |
| Shape of Base | Truncate |
| Apex | Mucronulate |
| Petiole length | 1-1.5 cm |
| Petiole color | Yellow-green 147D |

TABLE 2

| Differences with the comparison variety | | |
|---|---|---|
| | 'Zanmusunset' | 'Thor' |
| Flower size | 4.5 cm | 6.57 cm |
| Plant height | 40-45 cm | 30-35 cm |

The invention claimed is:

1. A new and distinct variety of *chrysanthemum* plant as described and illustrated.

* * * * *